United States Patent
von Schuckmann

(10) Patent No.: US 8,342,174 B2
(45) Date of Patent: *Jan. 1, 2013

(54) INHALER FOR POWDERY SUBSTANCES, IN PARTICULAR MEDICINAL SUBSTANCES

(75) Inventor: Alfred von Schuckmann, Kevelaer (DE)

(73) Assignee: Sanofi SA, Meyrin (CH)

( * ) Notice: Subject to any disclaimer, the term of this patent is extended or adjusted under 35 U.S.C. 154(b) by 1168 days.

This patent is subject to a terminal disclaimer.

(21) Appl. No.: 12/098,601

(22) Filed: Apr. 7, 2008

(65) Prior Publication Data

US 2008/0184999 A1    Aug. 7, 2008

Related U.S. Application Data

(62) Division of application No. 10/526,241, filed as application No. PCT/EP02/10353 on Sep. 16, 2002, now abandoned.

(51) Int. Cl.
*A61M 16/00* (2006.01)
(52) U.S. Cl. .......... 128/203.15; 128/200.24; 128/203.12
(58) Field of Classification Search .............. 128/200.11, 128/200.12, 200.14, 200.21, 200.23, 200.24, 128/203.13–203.16, 203.21–203.23
See application file for complete search history.

(56) References Cited

U.S. PATENT DOCUMENTS

| | | | | |
|---|---|---|---|---|
| 4,896,832 A | * | 1/1990 | Howlett | 239/322 |
| 5,239,992 A | * | 8/1993 | Bougamont et al. | 128/203.15 |
| 5,263,475 A | | 11/1993 | Altermatt et al. | |
| 5,429,122 A | * | 7/1995 | Zanen et al. | 128/203.15 |
| 5,447,151 A | * | 9/1995 | Bruna et al. | 128/203.15 |
| 5,765,552 A | * | 6/1998 | Zanen et al. | 128/203.15 |
| 6,321,747 B1 | * | 11/2001 | Dmitrovic et al. | 128/203.15 |
| 6,655,380 B1 | | 12/2003 | Andersson et al. | |
| 6,886,560 B1 | | 5/2005 | Seppälä | |
| 2004/0035421 A1 | | 2/2004 | Schuckmann | |
| 2008/0185000 A1 | * | 8/2008 | Schuckmann | 128/203.15 |
| 2008/0223365 A1 | * | 9/2008 | Von Schuckmann | 128/203.15 |

FOREIGN PATENT DOCUMENTS

| | | |
|---|---|---|
| DE | 4027391 | 3/1992 |
| DE | 4027391 A1 | 3/1992 |
| DE | 10047722 | 4/2002 |
| DE | 10047722 A1 | 4/2002 |
| EP | 0308100 | 3/1989 |
| EP | 0387222 | 9/1990 |
| EP | 0505321 | 9/1992 |

(Continued)

OTHER PUBLICATIONS

International search report, dated Feb. 27, 2003.

*Primary Examiner* — Annette Dixon
(74) *Attorney, Agent, or Firm* — McDonnell Boehnen Hulbert & Berghoff LLP

(57) ABSTRACT

An inhaler for powdery, in particular medical, substances is formed with a suction air channel, which leads to a mouthpiece. The inhaler also has a storage chamber for storing the substance and a linearly moving dosing chamber for apportioning a specified amount of substance from the storage chamber to a transfer point to the suction air flow. The aim of the invention is to obtain a structurally simple solution that makes it possible to eliminate adding an external air flow. To this end, a component of the suction air flow, which is located in the direction of extension of the dosing chamber, empties said dosing chamber.

11 Claims, 5 Drawing Sheets

FOREIGN PATENT DOCUMENTS

| | | |
|---|---|---|
| WO | 93/03782 | 3/1993 |
| WO | 97/30743 | 8/1997 |
| WO | 98/41256 | 9/1998 |
| WO | 01/21238 | 3/2001 |
| WO | 0121238 A2 | 3/2001 |
| WO | 02/26299 | 4/2002 |
| WO | 0226299 A1 | 4/2002 |
| WO | 2006/021546 | 3/2006 |

* cited by examiner

FIG 3
FIG 4
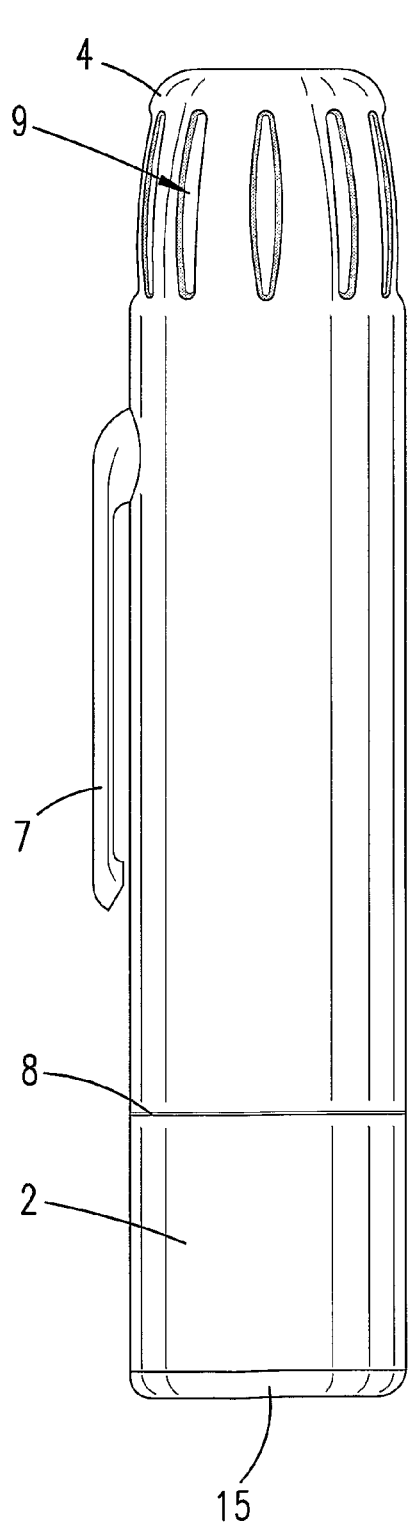
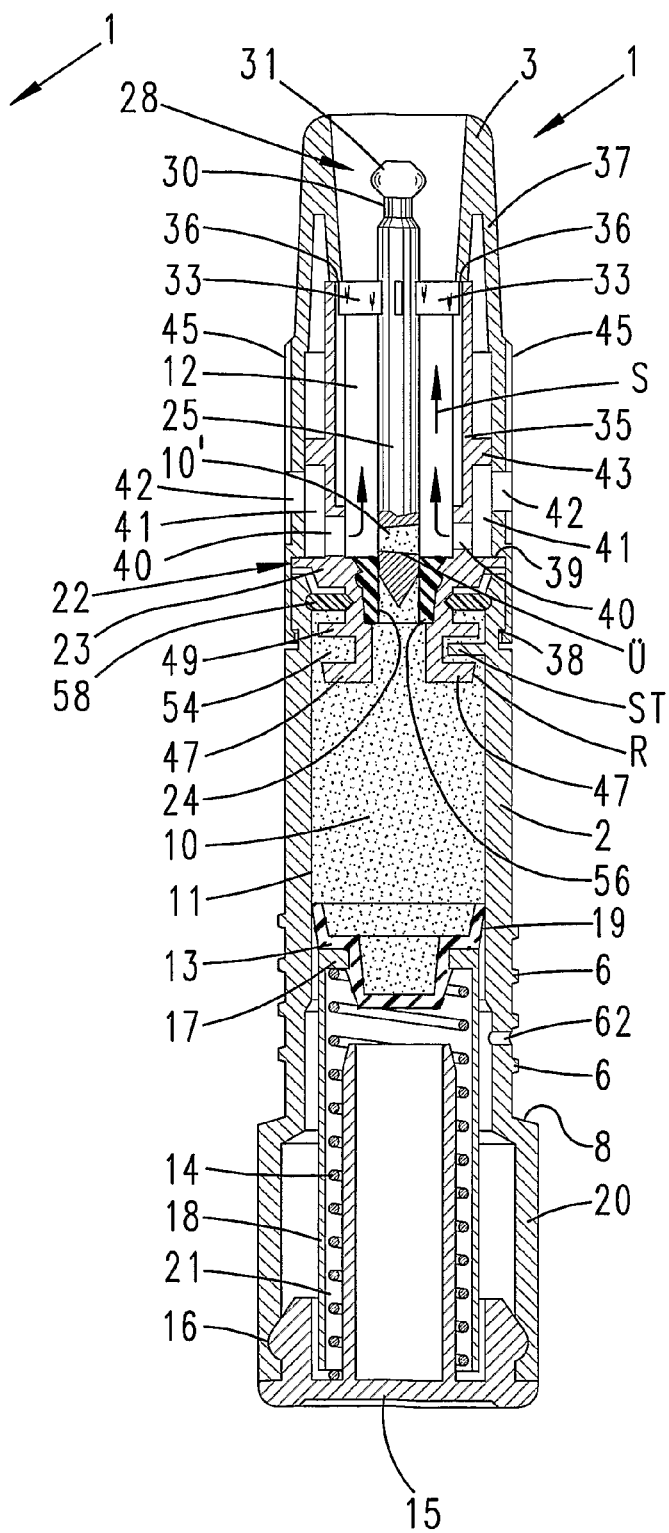

INHALER FOR POWDERY SUBSTANCES, IN PARTICULAR MEDICINAL SUBSTANCES

CROSS-REFERENCE TO RELATED APPLICATION

This application is a divisional of application Ser. No. 10/526,241, filed Nov. 21, 2005, now abandoned; which was a §371 national stage application of international application PCT/EP2002/01 0353, filed Sep. 16, 2002; the prior applications are herewith incorporated by reference in their entirety.

BACKGROUND OF THE INVENTION

Field of the Invention

The invention relates to an inhaler for powdery substances, in particular medicinal substances.

An inhaler of the generic type is described in U.S. Pat. No. 5,429,122. There, the amount of the substance to be delivered is transferred from a lower storage chamber to an upwardly movable dosing chamber. The dosing chamber is in the form of a ring-shaped groove in (or on) a linearly movable rod which is spring-loaded. A mandrel in the closure cap presses the rod into a retracted (lower) position. When the patient removes the cap, the rod is propelled rapidly upward into a ready-to-empty transfer position. The contents of the dosing chamber are advanced into the mouthpiece via a suction air stream created by the patient. A drawback is that the spring-loaded rapid upward propulsion of the rod tends to provide an incorrect dosage of the substance.

BRIEF SUMMARY OF THE INVENTION

It is accordingly an object of the invention to provide an inhaler for powdery, in particular medicinal, substances which overcomes the above-mentioned disadvantages of the heretofore-known devices and methods of this general type and which provides for an inhaler of simple construction which delivers into the transfer position a reproducibly uniform dose, ready to be delivered, when the closure cap is removed.

With the foregoing and other objects in view there is provided, in accordance with the invention, an inhaler for powdery substances, comprising:

a mouthpiece and a suction air channel leading to said mouthpiece;

a storage chamber for storing therein the powdery substance;

a linearly movable dipping plunger having formed therein a dosing chamber for apportioning a specific amount of substance from said storage chamber and moving the amount of substance to a transfer position for transfer to a suction air stream leading to said mouthpiece;

a closure cap for covering said mouthpiece, wherein when said closure cap is removed, said dipping plunger and said dosing chamber are moved into a ready-to-empty position;

a docking structure connecting said dipping plunger and said closure cap, said docking structure including a latching means configured to disengage upon an overload force and to reengage when said closure cap is returned in place.

In other words, the novel configuration achieves an inhaler which has a simple construction and which functions reliably and reproducibly. The "docking" is brought about with application of a steady, secure, and reliable force which the patient generates with the aid of screw threads. The patient does not need to apply a strong force, however, in order to achieve the ultimate release. The same applies to the screwing-on of the threaded closure cap (screw cap) into the closed position.

During the opening movement of the screw cap, no reversing acceleration forces can arise which might adversely affect the filling volume of the dosing chamber.

In accordance with the invention, the dipping plunger is disposed in a rotary part. Both the dipping plunger and the rotary part are moved by the screw cap.

It is further proposed that the dosing chamber is in the form of a transverse bore in the dipping plunger. With this arrangement, the dosing chamber is charged and is moved into the transfer position automatically and smoothly (so as not to cause disturbances which would affect dosing), by simple means, namely the normal opening (and closing) of the device. Both end positions can be reached reliably, without loss of the subject substance from the dosing chamber. The transverse through bore allows the removal of the substance from both ends. It is particularly advantageous if the transverse bore is (frusto)conical. The fluidics are such that the apportioned amount of the substance is removed more rapidly from the wider end, into the suction air stream.

To provide effective flow components in the direction of extent of the dosing chamber, it is significant that the dosing chamber is associated with an air passage which adjoins the air suction stream. This introduces a localized zone of underpressure. It is particularly advantageous if both ends of the dosing chamber are associated with respective neighboring air passages. In the case of a conically configured dosing chamber, it is further advantageous if the end of the dosing chamber having the larger open diameter is associated with an air passage of smaller diameter than said end of the dosing chamber, and the end of the dosing chamber having the smaller open diameter is associated with a second air passage of larger diameter than said smaller end. This tends to provide a larger underpressure on the end with the larger open diameter, to promote outflow in the direction in which, as a result of the steadily widening wall diameter of the dosing chamber, there is no frictional resistance. Because the air passages are formed in a rotary part having a generally vessel shape (cup shape) which guides the plunger, and said air passages are in fluid communication with the air inlets in the shell (lateral wall) of the mouthpiece, a good air path is continuously provided, as long as the dosing chamber is in the ready-to-empty transfer position. The said air inlets are located in the shell of the mouthpiece at locations chosen such that neither the patient's lips nor the hand by which the patient generally surroundingly holds the generally rod-shaped device will occlude said air inlets. A plurality of air inlets may be provided which are disposed at mutual distances, in order to further minimize the risk of air inlet occlusion.

To promote good distribution of the powdered substance in the suction air stream, the air passages may be axially displaced with respect to the air inlets, which latter may be closer to the mouthpiece. The effect of this is that, upon opening (of the device), the flow path will be U-shaped.

It has further been found advantageous if the generally cup-shaped bottom of the rotary part forms the cover for the storage chamber, and the center of said cup-shaped bottom has a guide opening for the dipping plunger. Said cup-shaped bottom thus has a dual function—serving as a direct or indirect cover, and serving as a guide for the dipping plunger.

It is also advantageous if the dipping plunger is rotationally connected to the rotary part by means of radial lobes. The required linear relative movement of the dipping plunger and the rotary part is provided by simple means comprising axial guide grooves in which the lobes are guided. In connection with this solution it is proposed to provide a detent or detents disposed on the mouthpiece, for limiting the available sliding excursion of the dipping plunger and defining the ready-to-empty transfer position of the dosing chamber (particularly, the transfer position of the base wall of said dosing chamber).

The positioning of the dipping plunger is controlled from the closure cap via a "docking point" (docking position structure) which is disposed at or near the mouthpiece end which docking position structure has latching means whereby the dipping plunger and the closure cap can interengage, which latching means can be disengaged by application of force ("overload") tending to pull (urge) the plunger and cap mutually apart. When the inhaler is re-closed, the dipping plunger and closure cap are mutually re-engaged by mutual thrust, giving rise to a "re-docking." The docking position structure serves to ensure correct positioning.

It is advantageous for purposes of sealing and guiding if the guide opening in the rotary part includes an elongated sealing ring ("sealing sleeve"), comprised of rubber material or the like, which is disposed around the cylindrical part of the dipping plunger. This elongated sealing provides a sufficiently large assembly opening.

The elongated sealing ring will also serve to clear away any powder substance which may settle on the shaft of the dipping plunger; this clearing function may help to avoid erroneous dosage.

Further sealing is provided in the dosing mechanism by a compressible sealing ring, also comprised of rubber or the like, which ring is inserted under prestressing between the interior wall of the storage chamber and the rotary part. This sealing ring is suitably compressively lodged in ring-shaped grooves in the two relevant pieces, wherewith the groove on the rotary part has a V-shaped profile and the groove on the storage chamber at the same altitude as the groove on the rotary part has a semicircular profile. The said V-profile groove also serves to guide the rotary part in rotational motion.

Other features which are considered as characteristic for the invention are set forth in the appended claims.

Although the invention is illustrated and described herein as embodied in inhaler for powdered, particularly medicinal, substances, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWINGS

FIG. 3 is a lateral view of the inhaler;

FIG. 4 a cross section analogous to FIG. 1, but with the closure cap removed and resultant displacement into the ready-to-empty transfer position;

DETAILED DESCRIPTION OF THE INVENTION

Figures 1, 2:
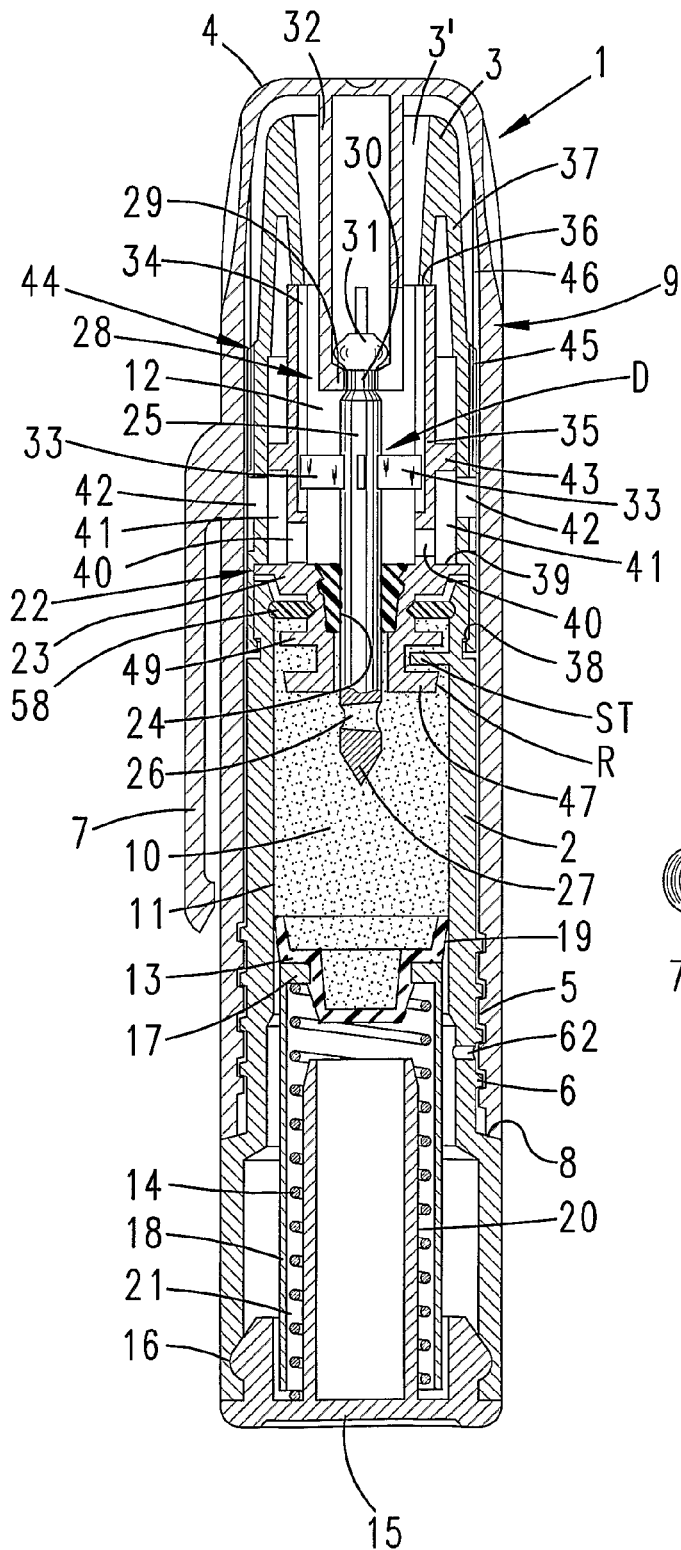
FIG. 1 is a vertical cross section of the inventive inhaler, enlarged, in the basic position with the closure cap closed.
FIG. 2 is a plan view of the inhaler.

Referring now to the figures of the drawing in detail, the inhaler illustrated in the drawings is a conveniently portable pocket device in the form of a short stick, with a shape-determining stepped cylindrical housing 2.

The generally tubular housing 2 undergoes a transition at the top end of the inhaler 1 into a built-in mouthpiece 3, which has an appropriate flattening for application of the patient's mouth. The housing 2 can be protectively engaged over by a cup-shaped closure cap 4.

The closure cap 4 is in the form of a screw cap, having an interior thread which engages a corresponding exterior thread 6 on the lateral wall of the housing 2. In the region of the mouthpiece, a clip 7 is formed on the closure cap 4.

The bottom end edge of the cup-shaped closure cap 4 sealingly abuts against an annular shoulder 8 which is provided as part of the abovementioned stepped structure of the cylindrical housing 2.

Utilizing the axial screw pitch of the threads (5, 6), the closure 4 also serves as an actuator member 9 to bring reproducible doses 10' of a powder substance 10, substance 10 in reproducible portions 10', which substance is accommodated in a storage chamber 11 of the housing 2 in an optionally refillable manner. The dosing device, respectively transporting the portion 10' to a transfer point Ü lying outside the storage chamber 11, is designated as a whole by D.

With respect to the material that can be dosed, it is a medical, powdery substance 10, for example of the nature that basic substances (lactose) capable of being transported by suction stream act as a vehicle for carrying the micronized fine particles of medicament sticking to their surface.

Provided downstream of the dosing device D is a so-called dispersing region, in which the user produces a suction air stream S which completely carries away the exactly apportioned amount 10' of the substance 10 at the transfer point Ü. The suction air channel leading to the mouthpiece 3 has the reference numeral 12.

The lower termination of the storage chamber 11 is formed by a cup-shaped pressure-exerting base 13. This is under spring loading in the direction of the mouthpiece 3. The corresponding compression spring has the reference numeral 14. It is supported by the bottom end winding on a base cap 15 closing the housing 2 there. Said base cap is in latching engagement with the portion of the housing 2 of larger cross-section there. The corresponding latching collar 16 engages in a matching annular groove of the housing 2.

The top end winding of the biased compression spring 14 loads an inner shoulder 17 of a hollow piston 18 of the piston-shaped device 13/18.

The stepped cup-shaped pressure-exerting base 13 is connected in a latching manner to the inner shoulder 17.

The cup edge of the pressure-exerting base 13 provides an annular lip 19, which on account of its rubber-elastic material wipes off the wall of the storage chamber 21 without any substance being lost.

Then a central standing spigot 20 extends from the base cap 15. Said standing spigot is hollow and, together with the hollow piston 18, forms a spring chamber 21 for the compression spring 14.

At the mouthpiece end, the storage chamber 11 terminates with a cup-shaped rotary part 22. This forms by its cup base the top 23 of the storage chamber 11 engaging over the housing 2.

A guiding opening 24 is left at the center of the top 23. This indirectly or directly formed guiding opening 24 receives a spindle 25, as the key component of the dosing device D. As a result of being appropriately configured, said spindle acts as a linearly moving dosing chamber 26 for the portion 10' to be lifted out, representing a plunger slide. It moves in the longitudinal center axis x-x of the substantially rotationally symmetrically configured inhaler 1.

Figure 7:
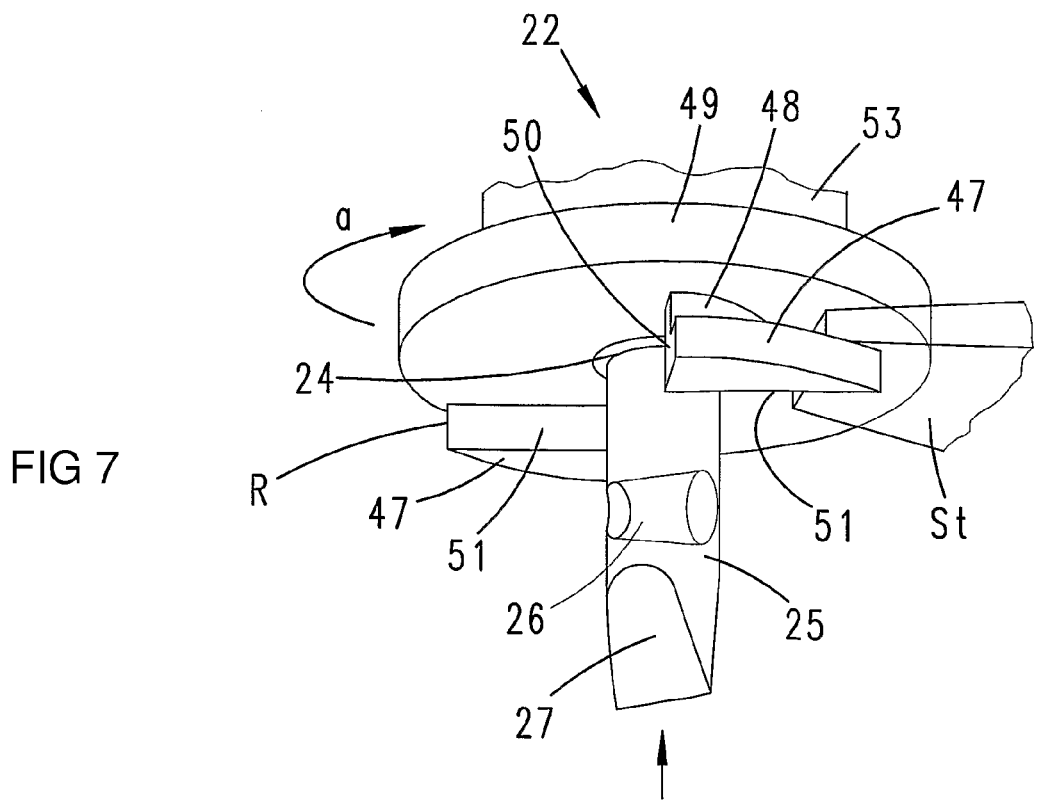
FIG. 7 is a perspective view from below of a detail of the rotary piece, showing the rotor and the stator, and showing the wedge-shaped configuration of the lower end of the dipping plunger.
Figure 8:
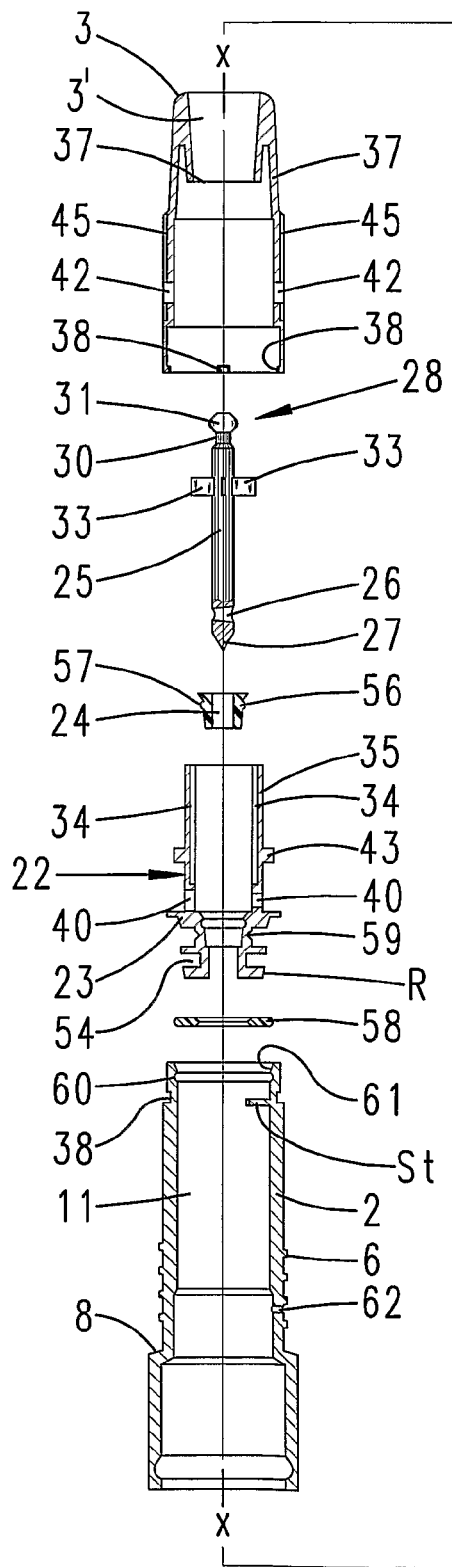
FIG. 8 is an exploded vertical cross sectional view of component parts of the inhaler, with the dipping plunger itself being shown in partial vertical cross section.
Figure 8:
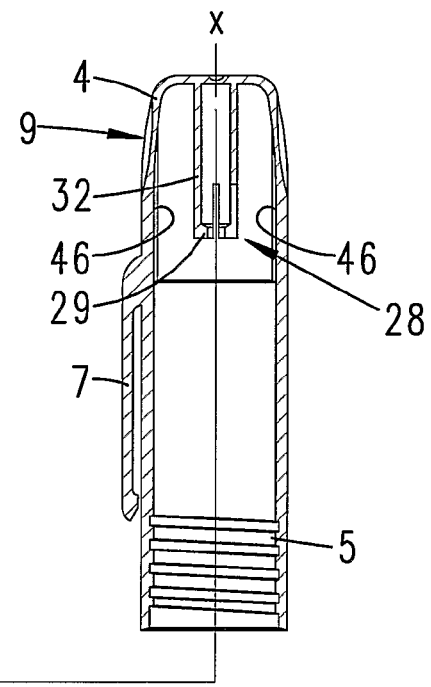
Figure 8:
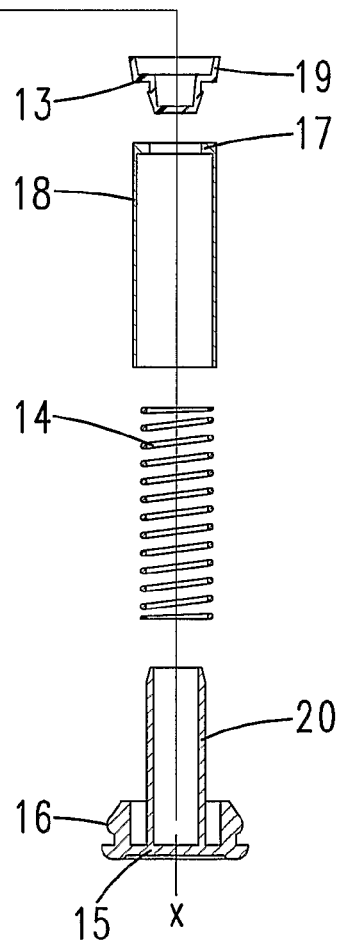

At its end remote from the mouthpiece 3, the spindle 25 forms a point similar to a screwdriver blade. On account of the co-rotation of the spindle 25, this has a loosening effect on the central region with respect to the mass of powdery substance 10. The blade 27, virtually resembling a pointed roof, has two mirror-symmetrical oblique flanks and, at the base, adjoins the cylindrical stem of the spindle 25. The oblique flanks enclose an angle of about 60°. The cylindrical base cross-section of the spindle 25 is retained in the region of the blade 27 (see FIG. 7). The stroke of the linearly moving dosing chamber 26 makes allowance in both end positions of the spindle 25 for the cross-section of the guiding opening 24 to be kept closed with a doctor-blade or wiping-off effect, filling the dosing chamber, over the length of said opening 24.

The end of the closure 4 toward the mouthpiece forms a docking point 28 between the spindle 25 and the closure cap 4. The latching means on the closure cap is in this case a ring of hooks capable of resilient deflection. Inwardly directed lugs 29 of the resilient tongues of the ring of hooks engage in a narrow waistlike annular groove 30 of the stem 25. In the outward direction, the annular groove 30 continues into a latching head 31. This can be overcome in both directions by the lugs 29. The accumulation of material forming the latching head is approximately lenticular.

The lugs 29, or their resilient tongues, are realized on a small tube 32 which protrudes into the mouthpiece opening 3' and extends from the inner side of the top of the closure 4. It is rooted therein.

The stem 25 is rotationally connected to the rotary part 22 by means of radial fins 33 formed in the manner of spokes. The fins 33 engage with their free end portions, crossing the suction air channel 12, in axial guiding slots 34 three are already sufficient—of the rotary part 22. The guiding slots 34, distributed at equal angles, are located on the inside of the cup wall 35 of the cup-shaped rotary part 22. The axial guiding slots 34 are, moreover, of such a length that the powder-drawing plunging stroke of the stem 25 out of a filling plane in the storage chamber 11 to the described transfer point U above the top 23 is ensured.

The defined ready-to-empty position of the dosing chamber 26 is obtained by an extension limiting stop of the spindle 25 that is provided by the mouthpiece 3. That is the extreme end of a turned-back wall of the mouthpiece 3, which in this way keeps the outlet of the guiding slots 34 closed.

The mouthpiece 3 acts via a lateral wall 37 in an anchoring manner on the neck of the housing 2. There, a latching point 38 is formed between the two parts 2, 3. It may be an irreversible latching point 38. Moreover, as can be gathered, the top 23 of the rotary part 22 is engaged over in a supported manner by an annular shoulder 39.

The dosing chamber 26 is realized as a transverse bore running substantially perpendicularly in relation to the longitudinal center axis x-x. Transferred into the ready-to-empty position, the dosing chamber 26 is in the effective region of the central suction air stream S. An air passage 40 adjoining the suction air channel 12 is associated with the dosing chamber 26. Said air passage is formed in the cup wall 35 of the rotary part 22. It comprises radial bores. They extend in the vicinity of the base of the cup-shaped rotary part 22, that is at the height of, or just above, the upper side of the top 23.

It can be gathered that such an air passage 40 is provided upstream and at a radial spacing from both open ends of the dosing chamber 26. One precaution in this connection is that associated with the larger clear diameter end of the dosing chamber 26 formed by a conical transverse bore is an air passage 40 of a smaller diameter than it and associated with the smaller clear diameter end of the dosing chamber 26 is an air passage 40 of a larger diameter than it. This produces a greater reduced pressure with a predominant discharging effect with respect to the administered portion 10' downstream of the air passage 40 of smaller diameter. Nevertheless, the discharge, i.e., emptying of the dosing chamber 26, takes place from both ends.

The passages 40 formed on the cup-shaped rotary part 22, guiding the stem 25 in a sealed manner, are also in flow communication via a rearward annular space 41 with air inlets 42 which are at a radial distance. These air inlets 42 are also configured as bores and provide the connection to the atmosphere. Said annular space 41 is located between the outer side of the cup wall 35 of the cup-shaped rotary part 22 and the inner side of the lateral wall 37 of the mouthpiece 3.

It can be gathered that the air passages 40 are disposed axially offset in relation to the air inlets 42. The air inlets 42 lie closer to the mouthpiece 3. The described spatial distancing leads to an initially contra-acting inflow of sucked-in air following on from the main suction air stream S. This and the fact that a component of the suction air stream S lying in the direction in which the dosing chamber 26 extends is built up has the effect that the dosing chamber 26 is completely emptied. The user inhales a precise dose each time. The transfer point Ü is provided here by the base portion of the dosing chamber 26.

Conducive to the corresponding emptying is the special way developed here of keeping the powder substance 30 ready in the drawing region: this is so because conditions are created here to ensure the aimed-for isostructural or homogeneous "packing" of the dosing chamber 26, fed from a surrounding area where the substance has been loosened. The rotary part 22 is used in particular for this purpose, by way of a development. It has a rotor R acting in the upper region of the storage chamber 11. A stator ST is associated with said rotor. Using the rotation of the rotary part 22, not only is a loosening effect obtained but at the same time also a scooping effect acting so as to carry powder into the dosing chamber 26 when the rotary part 22 is reversed in its rotation, i.e. when the closure cap 4 is unscrewed, using the same as an actuating handle 9. The corresponding entrainment is also obtained with respect to the spindle 25, which is rotationally secured radially by means of the fins 33, so that there is no displacement of the axis of the dosing chamber 26 in relation to the air passages 40. Even the lateral wall 37 could be included in the rotational fixing by connecting means with positive engagement. Generally, even co-rotation with frictional engagement is sufficient, for example by means of the annular collar 43 keeping the annular space 41 closed toward the mouthpiece end. Said annular collar extends from the lateral wall of the cup wall 35 and lies with its outer edge against the inner side of the lateral wall 37 of the mouthpiece 3.

As FIGS. 1 and 4 reveal, the co-rotation between the mouthpiece 3 and the closure cap 4, lifting off by an unscrewing action, takes place by a claw coupling 44 between the two. This comprises a longitudinal toothing 45 on the lateral wall 37 of the mouthpiece 3, which longitudinal toothing engages in corresponding tooth gaps 46 on the inner side of the closure cap 43.

The scoop is formed by two rotor blades 47. These have a basically sickle-shaped outline. The two rotor blades 47 are located diametrically opposite with respect to the longitudinal center axis x-x of the inhaler 1. They are mounted on axially running webs 48 spaced at a distance from the center. The webs are rooted in the underside of an arm or an annular disk 49 of the rotary part 22 providing the rotor R.

Figure 6:
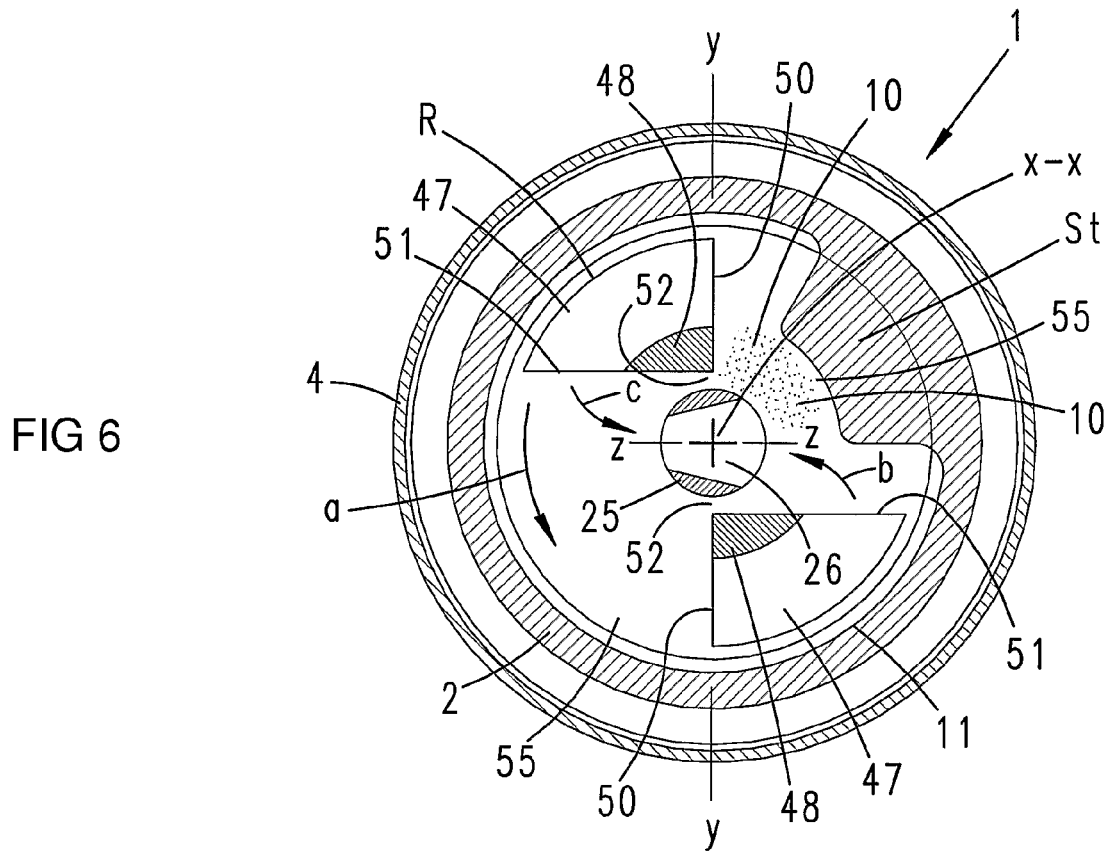
FIG. 6 is a cross section through line VI-VI of FIG. 5.

The freely extending rotor the base or the top 23 of storage chamber side are blades 47 protruding from the rotary part 22 on the positioned diametrically opposite in such a way that they are sufficiently spaced apart in the circumferential direction. Geometrically, they substantially take up a quarter sector of the circular cross-section of the storage chamber 11. Reference should be made to FIG. 6. The two rotor blades 47 each have a flank 50 aligned radially with the center of the spindle 25 and each have a scoop flank 51 lying at right angles thereto. It runs at a distance from the lateral wall of the spindle 25 in such a way as to leave a gap. The gap has the symbol 52. In this way, an abrasive effect is avoided. It can be gathered that the flanks 50 are diametrically opposed. The common diametral line of the flanks 50 is designated in FIG. 6 by y-y. The spatially parallel scoop flanks 51 extend perpendicularly in relation to the diametral line y-y and spatially parallel to the axis z-z of the transverse bore of the dosing chamber 26, which in turn coincides with the axis of the bore of the air passages 40.

The annular disk 49 or two arms in which the rotor blades 47 are rooted continues via an annular wall 53 into the top 23 of the rotary part 22.

Figure 5:
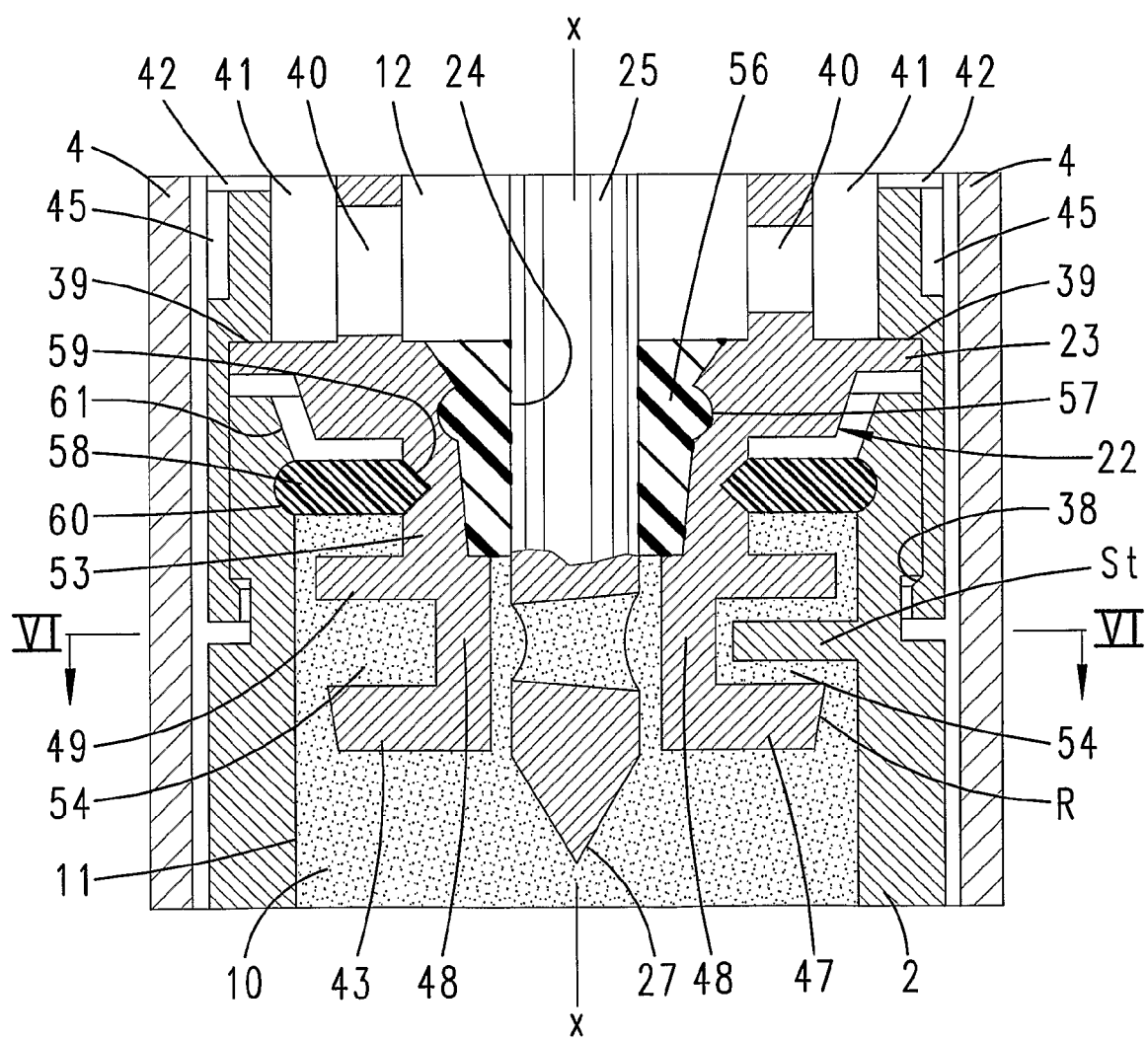
FIG. 5 is an enlarged view of a detail analogous to FIG. 1, wherein the dipping plunger is in an intermediate position, with the dosing chamber being disposed at the same altitude as the stator.

FIG. 5 illustrates particularly clearly that the rotor R engages underneath the stator ST in such a way that the stator ST is formed as a projection protruding radially inward from the inside wall of the storage chamber 11 and extending freely into a rotational path 54 of the rotor R. It can be gathered that the rotational path 54 is axially limited by the underside of the annular disk 49 of the rotary part 22 and the inner side of the rotor blades 47 facing it. The axial distance forming the rotational path is significantly greater than the thickness of the stator ST, that is the projection, measured in this direction. Therefore, mechanical loads with respect to the frictionally sensitive powdery substance 10 to be discharged do not occur here either.

The stator ST has a trapezoidal outline. The arcuate base is rooted in the inside wall of the storage chamber 11. The base is dimensioned such that the stator ST narrowing radially inward in its surface area lies in outline beneath the quarter sector, leaving an interspace 55 between two rotor blades 47. As FIG. 6 reveals, this at the same time provides an adequate mounting opening for the stator to engage in the rotational path 54.

The radial projection of the stator ST in the inward direction is of such a radial length that the plateau of the trapezoid ends before the outer side of the web 48, likewise forming a gap.

The scooping effect is clear from FIG. 6, if the arrows are observed. Arrow a indicates the direction of reversed rotation of the rotary part 22. The scoop flanks 51 therefore act as a face pushing the powder lying in front of it. Arrow b shows the approaching scooping-in direction with respect to the end of the dosing chamber 26 having the larger clear diameter. Arrow c indicates the corresponding action at the other rotor blade 47, that is here also with respect to the scooping action of the scoop flank 51. The stator ST then stands as it were as a fixed chicane in the way of the rotational path 54. The powdery substance 10 is displaced with a rapidly chamber-filling effect by the scoop flank 51 lying closer to the directing-in flank of the trapezoid, so that, as already stated, consistent filling conditions always occur. The dosing chamber 26 moves in an ascending manner through the zone of the dosing device D in a number of rotations until it has reached with its transfer point Ü the upper side of the top 23 of the cup-shaped rotary part 22.

There is also no entrainment of powder material that may be adhering to the lateral surface of the spindle, as a result of the guiding opening 24 with a wiping-off effect. Said opening is not formed directly by the rotary part 22, but by a sealing bush 56 lining this passage. Said sealing bush consists of rubber-elastic material and is held by being clipped into the top 23 by latching means 57. In terms of its plane, it reaches at the top up to the height of the upper side of the annular disk 49.

However, there is also no radially outer escape hole for powder losses, since there is likewise a sealing element between the rotary part 22 and the housing 2 forming the storage chamber 11. This is achieved by a sealing ring 58 of rubber-elastic material inserted between the inside wall of the storage chamber 11 and the rotary part 22. Said sealing ring 58 is inserted under preloading. The sealing ring 58 is snap-fitted in annular grooves of both parts 2, 22. The annular groove located on the annular part 22 has the reference numeral 59. It is realized as a V-shaped notched groove. The opening angle of the annular groove 59 lying in the region of the annular wall 53 is about 90° The groove contour has a centering and rotationally guiding effect. The other annular groove 60, lying at the same height, is located on the inner side of the housing 2, to be precise in the upper inlet region of the storage chamber 11. Here there is a semicircular shape with respect to the cross-section of the peripheral annular groove 60. Mounting is made easier by a rotationally symmetrical run-up slope 61 provided in front of the annular groove 60.

The spindle 25, formed as a lifting spindle, can be varied with respect to the volume of its dosing chamber 26, i.e. the key component of the dosing device D merely has to be exchanged to achieve a different, precisely reproducible dosing of portions 10'.

The pressure-exerting base 13, acting in the manner of a piston, is not impaired in its ability to move with respect to the cylinder space, provided by the central portion of the housing 2, since there the housing has an air-equalizing opening 62 lying to the rear of the annular lip 19.

The cup-shaped pressure-exerting base 13 has a central indentation, directed away from the storage chamber 11. It is of such a depth on the inside that the end portion of the spindle 25 projecting axially downward beyond the rotor blades 47 in the basic position is accommodated in it.

All features disclosed are (in themselves) pertinent to the invention. The disclosure content of the associated/attached priority documents (copy of the prior patent application) is also hereby incorporated in full in the disclosure of the application, including for the purpose of incorporating features of these documents in claims of the present application.

The invention claimed is:

1. An inhaler for powdery substances, comprising:
 a rotatable mouthpiece connected to a stationary housing, where the housing has external threads;
 a rotary part rotationally fixed with the mouthpiece containing a suction air channel leading to the mouthpiece;
 a storage chamber for storing therein the powdery substance;
 a linearly movable non-biased dipping plunger rotationally fixed with the rotary part having formed therein at one end a dosing chamber for apportioning a specific amount of substance from the storage chamber and moving the amount of substance to a transfer position in fluid communication with the suction air channel, where the dipping plunger has an end opposite the dosing chamber having a latching head; and
 a closure cap for covering the mouthpiece, where the closure cap has an interior portion containing internal threads configured to engage the external threads on the housing and a docking structure configured to removably latch onto the latching head such that when the closure cap is unscrewed the docking structure pulls the dipping plunger and the dosing chamber into a ready-to-empty position and when the cap is removed the docking structure disengages from the latching head.

2. The inhaler according to claim 1, wherein the dipping plunger is slidably disposed in the rotary part, and an available sliding travel of the dipping plunger is limited by one or more detents, and wherein, when the closure cap is subjected to screwing movement, the dipping plunger is concurrently moved via longitudinal toothing and is eventually moved such that the dosing chamber is brought into the transfer position.

3. The inhaler according to claim 2, wherein the rotary part is formed with a guide opening and wherein the guide opening is lined with a sealing sleeve disposed around a cylindrical part of the dipping plunger.

4. The inhaler according to claim 1, wherein the dosing chamber is a conical transverse bore through the dipping plunger having two open ends for emptying from the two ends via a component of a suction air stream effective in a direction of the dosing chamber, and wherein each of the two open ends of the dosing chamber is in fluid communication with the suction air channel.

5. The inhaler according to claim 4, wherein the two open ends of the dosing chamber include a first end with a relatively larger open diameter associated with an air passage of a relatively smaller diameter than the first end, and a second end with a relatively smaller open diameter associated with an air passage of a relatively larger diameter than the second end.

6. The inhaler according to claim 5, which comprises a rotary part having the air passages formed therein, the rotary part having a generally vessel shape that guides the dipping plunger, and the air passages are in fluid communication with air inlets formed in a lateral wall of the mouthpiece.

7. The inhaler according to claim 6, wherein the air passages are displaced with respect to the air inlets in an axial direction of the inhaler.

8. The inhaler according to claim 1, which comprises a stroke-limiting detent for the dipping plunger, the said detent being disposed on the mouthpiece and having a base wall section defining the transfer position of the dosing chamber.

9. The inhaler according to claim 1, which comprises a compressible sealing ring inserted under pre-stressing between an interior wall of the storage chamber and the rotary part.

10. The inhaler according to claim 9, wherein the rotary part has a V-shaped annular groove formed therein and a wall of the storage chamber has an annular groove with a semicircular profile formed therein at an even altitude with the Vshaped groove on the rotary part, and the compressible sealing ring iscompressively lodged in the annular grooves.

11. The inhaler of claim 1 where the mouthpiece has toothing configured to engage the interior of the cap closure such that rotation of the cap when unscrewed from the housing causes the mouthpiece to rotate therewith.

* * * * *